United States Patent
Crosby

(10) Patent No.: US 6,770,487 B2
(45) Date of Patent: Aug. 3, 2004

(54) BAR CODE READABLE DIAGNOSTIC STRIP TEST

(75) Inventor: Peter A. Crosby, Denver, CO (US)

(73) Assignee: Ischemia Technologies, Inc., Arvada, CO (US)

(*) Notice: Subject to any disclaimer, the term of this patent is extended or adjusted under 35 U.S.C. 154(b) by 171 days.

(21) Appl. No.: 09/846,411

(22) Filed: May 1, 2001

(65) Prior Publication Data

US 2003/0124738 A1 Jul. 3, 2003

(51) Int. Cl.⁷ .............................................. G01N 33/53
(52) U.S. Cl. ...................... 436/518; 435/7.1; 435/2; 435/5; 435/7.21; 435/7.32; 435/239; 435/287.2; 435/207.7; 435/805; 435/810; 435/970; 436/513; 436/512; 436/518; 436/531; 436/526; 436/806; 422/56
(58) Field of Search .................. 435/7.1, 2, 5, 7.21, 435/7.32, 239, 803, 287.2, 207.7, 805, 810, 970; 436/513, 512, 518, 531, 526, 806; 422/56

(56) References Cited

U.S. PATENT DOCUMENTS

| | | | |
|---|---|---|---|
| 4,509,859 A | | 4/1985 | Markart et al. |
| 4,510,383 A | | 4/1985 | Ruppender |
| 4,592,893 A | | 6/1986 | Poppe et al. |
| 5,569,608 A | * | 10/1996 | Sommer |
| 5,602,040 A | | 2/1997 | May et al. |
| 5,710,008 A | | 1/1998 | Jackowski |
| 5,976,895 A | | 11/1999 | Cipkowski |
| 6,036,092 A | * | 3/2000 | Lappe |
| 6,087,184 A | * | 7/2000 | Magginetti et al. |
| 6,136,549 A | * | 10/2000 | Feistel |
| 6,149,719 A | | 11/2000 | Houle |
| 6,171,870 B1 | * | 1/2001 | Freitag |
| 6,203,069 B1 | | 3/2001 | Outwater et al. |
| 6,335,205 B1 | * | 1/2002 | Bausback |
| 6,394,952 B1 | | 5/2002 | Anderson et al. |
| 6,410,341 B1 | * | 6/2002 | Freitag et al. |

* cited by examiner

Primary Examiner—Bao Thuy L. Nguyen
(74) Attorney, Agent, or Firm—Swanson & Bratschun LLC

(57) ABSTRACT

Diagnostic test devices, including diagnostic strip tests, are provided in which identifying information and the test result are machine-readable. Also provided are methods for obtaining identifying information and test results from the diagnostic test devices.

26 Claims, 2 Drawing Sheets

BAR CODE READABLE DIAGNOSTIC STRIP TEST

FIELD OF THE INVENTION

The invention is in the field of in vitro diagnostics, and specifically "dip stick" type diagnostic strip tests.

BACKGROUND OF THE INVENTION

So called "strip tests" are used for a wide variety of diagnostic applications. A strip test consists of an elongated rectangular component, often of paper, nitrocellulose or other porous inert material, upon which are printed stripes or layers of chemical compounds. It is generally used with a body fluid sample, e.g., urine or blood. One end of the strip is dipped into the sample, and the fluid is drawn along the strip by capillary action. As the sample passes the zones of chemical compounds, chemical reactions occur which may result in a color change, thus causing the appearance of one or more stripes. Often, a further stripe of color is used as quality control to indicate that the reaction has proceeded to completion.

The technology for such strip tests is well known in the art, and includes immunodiagnostic, enzymatic, lateral flow immunochromatography, or chemistry type reactions. Examples of strip test applications include single tests such as pregnancy (see, for example, U.S. Pat. No. 5,602,040 "Assays" by May et al., 1997); multiple simultaneous tests on a single strip such as for diagnosing patients with chest pain of suspected cardiac origin (see for example U.S. Pat. No. 5,710,008 "Method and Device for Diagnosing and Distinguishing Chest Pain in Early Onset thereof" by Jackowski, 1998); and apparatus for performing simultaneous single tests on multiple strips such as for drugs of abuse (see for example U.S. Pat. No. 5,976,895 "Device for the Collection, Testing and Shipment of Body Fluid Samples" by Cipkowski, 1999).

Strip tests can be used for qualitative yes/no results (such as a pregnancy test), or may be used to provide quantitative information, such the strip tests for blood glucose commonly used by diabetic patients. A quantitative test may use the intensity of generation of a color, or the color itself to indicate the result, or perhaps the generation of a different number of optically readable bands to indicate the result. The results can be read by a human operator by comparing the color to a printed reference, or a better quantitative result can be obtained by using an instrument to precisely determine the intensity or color of the test band. See for example U.S. Pat. No. 4,509,859, "Apparatus for the Optoelectronic Evaluation of Test Strips," E. Markart et al., Apr. 9, 1985.

It is important in clinical applications of strip tests to include with the strip information about the lot number, calibration constants, date of expiry and the like. This may be printed in text on the strip or package and read by a human operator. However, it is also possible to encode much of this information in a bar code which is printed onto the front or back of the strip test. See, for example, U.S. Pat. No. 4,592,893, "Analysis Test Strip", Poppe et al., Jun. 3, 1986. Such information can be read using a conventional bar code scanner, or by a special purpose device such as described by Ruppender in U.S. Pat. No. 4,510,383 "Device for Optical Identification of a Coding on a Diagnostic Test Strip", Apr. 9, 1985.

Such information might be useful when the test is done as part of a hospital environment and the calibration and other data as well as the results must be entered into a hospital Laboratory Information System (LIS). Many hospitals now have some sort of LIS to allow hospital wide ready access to laboratory and other diagnostic tests on the hospital computer network. Most modem laboratory based IVD instruments include hardware and software for automatic communication of test results to the hospital wide LIS. Strip test results, if required to be included in the LIS, currently suffer from the disadvantage that such results must be entered into the LIS manually. Manual entry of test results can potentially be time-consuming, limiting the efficiency of clinical personnel who must enter the data. Manual entry also introduces an opportunity for error or even the possibility the results are not entered at all. These errors can compromise a patient's safety or clinical outcome because of missing diagnostic data which could be used to affect clinical medical care. Accordingly, there remains a need for improved entry of test data into LIS-type systems.

SUMMARY OF THE INVENTION

The present invention provides a diagnostic test device comprising at least one flow path, each flow path comprising a sample zone for application of a fluid sample, at least one test zone in fluid communication with the sample zone, the test zone of each flow path providing reagents necessary for performing an assay for the presence of an analyte, whereby an analyte assay result may be obtained, and machine-readable information comprising identifying information and said analyte assay result.

The present invention also provides a diagnostic strip test comprising at least one flow path, each flow path comprising a sample zone for application of a fluid sample, at least one test zone in fluid communication with the sample zone, the test zone of each flow path providing reagents necessary for performing an assay for the presence of an analyte, whereby an analyte assay result may be obtained, and machine-readable information comprising identifying information and said analyte assay result, wherein the test zone comprises a portion of the machine-readable information.

The present invention provides strip tests for a single analyte or multiple analytes. The strip tests are suitable for the semi-quantitative detection of an analyte if a plurality of test zones indicates a positive result only in the presence of a given concentration or amount of analyte. The bar code may be a standard barcode which is a series of vertical bars, or a two-dimensional barcode, or other technology for optically encoding information. Furthermore, the bar code may be visible or invisible.

The invention also provides a method for obtaining identifying information and the analyte assay result of a diagnostic test, comprising the steps of providing a diagnostic test device comprising: a sample zone for application of a fluid sample, at least one test zone providing reagents necessary for performing an assay for the analyte, whereby the analyte assay result may be obtained, and machine-readable information comprising identifying information and the analyte assay result; performing the analyte assay, and machine reading the machine-readable information, whereby the identifying information and analyte assay result may be obtained.

The present invention further provides a method for obtaining identifying information and the analyte assay result of a diagnostic strip test, comprising the steps of providing a diagnostic strip test of the present invention, performing the analyte assay, and machine reading the machine-readable information, whereby the diagnostic strip test identifying information and analyte assay result may be obtained.

Each reference cited herein is incorporated in its entirety by reference.

DETAILED DESCRIPTION OF THE PREFERRED EMBODIMENT

The present invention provides a diagnostic test device comprising a sample zone for application of a fluid sample, at least one test zone providing reagents necessary for performing an assay for the presence of a desired analyte, whereby an analyte assay result may be obtained, and machine-readable information comprising identifying information and the analyte assay result.

It is to be noted that the term "a" or "an" entity refers to one or more of that entity; for example, a test zone refers to one or more test zones. As such, the terms "a" (or "an"), "one or more" and "at least one" can be used interchangeably herein.

Figure 1:
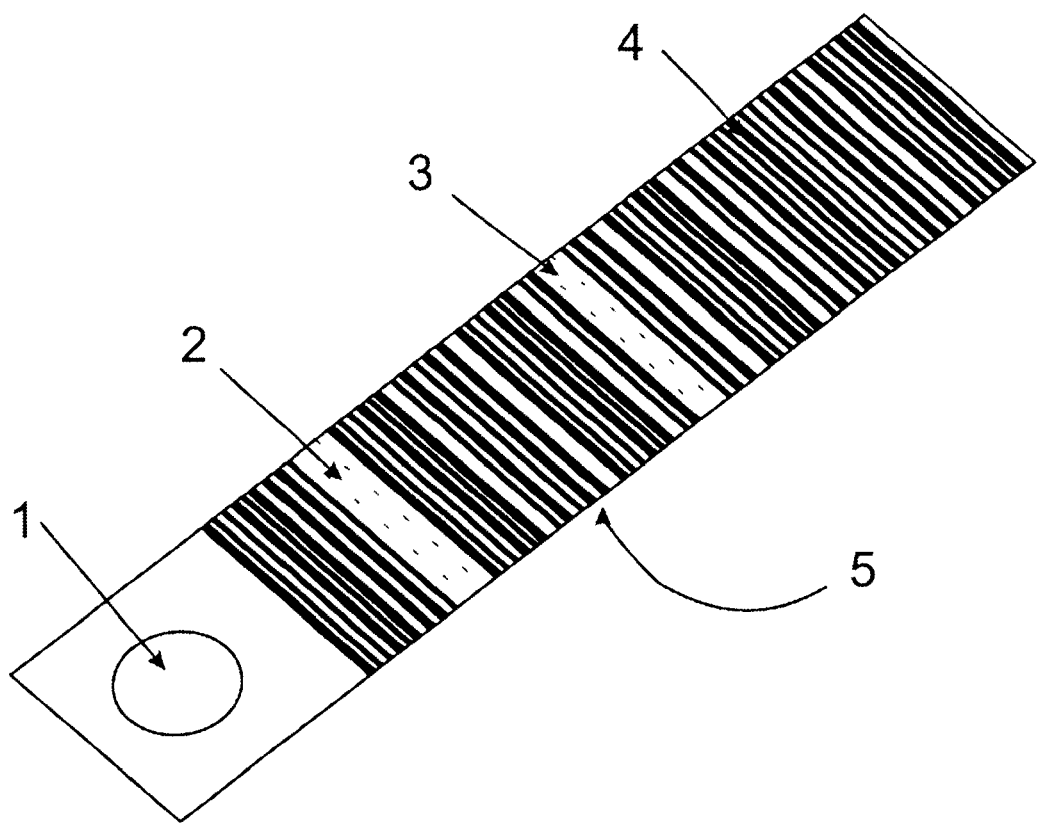
FIG. 1 shows a bar code printed strip test for a single assay.

One embodiment is illustrated in FIG. 1. While the Figures show diagnostic strip tests, it is to be understood that other diagnostic test devices may be adapted for use in the present invention by those skilled in the art. While the Figures show diagnostic strip tests having only one flow path for simplicity, it is to be understood that embodiments comprising more than one flow path are also included within the scope of this invention. A strip test assay as is well known in the art is provided with machine-readable information, for example, a bar code (4). As used herein, bar code refers to a printed horizontal strip of vertical bars of varying widths, groups of which represent decimal digits or other information and are used for identification purposes. The vertical bars are also referred to herein as stripes. Bar codes are read by a bar code reader or scanner and the code interpreted either through software or a hardware decoder. The bar code may be printed in inert ink, or might be printed on a transparent overlay so as not to interfere with the test itself. The bar code also may printed in invisible ink. As used herein, "invisible" ink is ink that is not visible with the human eye when illuminated with light in the visible spectrum. Examples of invisible ink bar codes and their use are described in U.S. Pat. No. 6,203,069. Invisible ink may be ultraviolet (UV) ink or infrared (IR) ink. The UV or IR ink produces visible light when illuminated with a UV or IR light source, respectively. Other invisible inks known in the art may also be used with the appropriate readers, for example, the metal phthalocyanine fluorophores disclosed in U.S. Pat. No. 6,149,719. U.S. Pat. No. 6,149,719 and every other reference cited herein is incorporated by reference in its entirety.

Although the use of a bar code for encoding machine-readable information is described herein, other forms of machine-readable information can also be used in the present invention. Another type of machine-readable information is Magnetic Ink Character Recognition (MICR). MICR is character recognition system using special ink and characters which can be magnetized and read automatically. MICR is used most often in the banking industry where it is used to print details on checks to enable automatic processing. In the present invention, a test zone could be in the shape of an MICR character. A positive test result would make the character-shaped test zone machine-readable and, optionally, visible. Optical character recognition is another type of machine readable information, in which the electronic identification and digital encoding of printed or handwritten characters is accomplished by means of an optical scanner and specialized software. Machine-readable information can also include, for example, radioactivity. Other types of machine-readable information and their adaptation to the present invention will be obvious to one of skill in the art.

The machine-readable information includes identifying information such as the type of test, the lot number, expiration date, calibration factors, and the like. The sample is applied at one end at the sample zone, either by dipping the strip into the sample, or by applying the sample to the sample zone (1). The apparatus may also include means for processing the fluid sample, for example a filter to remove cells from a blood sample. As the fluid sample migrates by capillary action up the strip test, first the test zone (2) is wetted by the fluid, and then the optional quality control zone (3), used to indicate that the test has run to completion.

As used herein, "zone" will refer to a discrete situs containing one or more reagents and positioned along the flow path of a particular assay. A sample is any solution, synthetic or natural, containing a substance suspected of being a member of a specific binding pair, such as an analyte, including body fluids such as, for example, whole blood, blood fractions such as serum and plasma, synovial fluid, cerebro-spinal fluid, amniotic fluid, semen, cervical mucus, sputum, saliva, gingival fluid, urine, and the like, and aqueous or water soluble solutions of natural or synthetic compounds, particularly, compounds that are potential therapeutic drugs, and it is desired to determine if the compound binds to a specific receptor. The amount of the sample depends on the nature of the sample and the analyte contained therein. For fluid samples such as whole blood, saliva, urine and the like the amount of the sample is usually about 100 to 5000 nanoliters, more usually, about 500 to 1000 nanoliters. The sample can be pretreated and can be prepared in any convenient medium.

A test zone contains a nondiffusively bound reagent for the detection of the desired analyte. Nondiffusively bound will be used interchangeably with the word "immobilized" to describe reagents that are stably retained in a particular zone under conditions of use. Reagents can be immobilized via any suitable technique as will be apparent to those skilled in the art. Direct attachment methods include nondiffusive adsorption, nondiffusive absorption, attachment to microparticles that are themselves entrapped in the appropriate position, and covalent binding, such as by use of cyanogen bromide, carbonyl diimidazole, or glutaraldehyde. In a preferred embodiment, the test zone is in the shape of a bar code stripe. The width of the stripe will be chosen such that the stripe, when present, encodes particular information either alone or in combination with the other stripes present in the bar code. If the test result is positive, then the test zone will display a positive result; i.e., it will change color, altering the bar code by "adding" an additional stripe. In a similar embodiment, the test zone might be configured such that detection of an analyte will result in disappearance of the test zone stripe, such that the data encoded in the bar code is changed as well.

In general, the sample is suspected of containing an analyte. An analyte will typically be one member of a specific binding pair, while the test zone of the strip test will contain a second member of a specific binding pair. A member of a specific binding pair can include, for example, substances such as antigens, antibodies, receptors, peptides, proteins, ligands, single-stranded and double-stranded DNA, oligonucleotides, cDNA, mRNA, RNA, and the like. The analyte can be monovalent (monoepitopic) or polyvalent (polyepitopic), synthetic or natural, antigenic or haptenic, and may be a single compound or plurality of compounds which share at least one common epitopic or determinant site. The analyte can be a part of a cell such as bacteria or a cell bearing a blood group antigen such as A, B, D, etc., or an HLA antigen, plasma membrane receptors or a microorganism, e.g., bacterium, fungus, protozoan, or virus. The analyte can also be a chemical compound, such as a drug or a metabolite thereof. It should be understood that often the specific binding pair itself will not be detectable by visual or machine-assisted readout, but can be made so by techniques known to those skilled in the art. For example, if the analyte is an antibody, and it is bound to an antigen immobilized in the test zone, the antibody may be detected by a secondary antibody conjugated to an enzyme which can hydrolyze a colorless substrate that produces a colored product. The detection of a specific binding pair may occur simultaneously with the test, or may occur in one or more subsequent steps, depending on the test.

The formation of a specific binding pair between the analyte of interest and the reagent immobilized in the test zone may be detected by visual readout or machine-assisted readout. In a preferred embodiment, the formation of a specific binding pair in the test zone is detected by a visible color change. When the test zone is in the shape of a bar code stripe, a detectable indication which becomes part of the bar code and serves to encode test results. The detectable indication can be a color change, if a visible result is desired. In other embodiments, the detectable indication is created by enzymes, fluorophores, chromophores, radioisotopes, dyes, colloidal gold, colloidal carbon, latex particles, and chemiluminescent agents. In some embodiments, the detectable indication is not visible to the eye, but is detected by suitable equipment. Such is the case when the specific binding pair is fluorescent, or radioactive, for example.

The diagnostic test devices of the present invention may optionally comprise a quality control zone comprising an indicator reagent for confirming the completion of the respective assay. In a preferred embodiment, the quality control zone is in the shape of a bar code stripe. The indicator reagent is typically a material that is sensitive to the presence of the sample. It is generally a material that will change color in response to the presence of some moiety in the sample solution. Examples of such a reagent include, but are not limited to, pH indicator dyes, dyes sensitive to the presence of proteins, and dyes sensitive to hydration states. A successful test run will result in a detectable indication within the quality control zone, also called a quality control confirmation. The detectable indication may be visible, and may also be machine-readable.

Once the required time for the test has expired, the results may appear in a visible form. In general the presence of a detectable indication of the presence of the analyte in the test zone will correlate with a positive result, but it is to be understood that the absence of such a detectable indication may also be a desired result. More importantly, the presence or absence of the detectable indication in the test zone, is encoded into the data read by a suitable machine, such as a bar code reader. Bar code readers, encoding technologies, and methods of use are well known in the art. The bar code reader could be implemented as a hand held wand, a specialized instrument, or a stationary device such as used in supermarket checkouts. In this way, the identifying information for the test, the test result, and optionally, quality control confirmation, are machine-read, preventing the possibility of erroneous data entry as may happen if the result and other information are entered separately.

If there is insufficient space to encode all the required information on one side of the strip test, then it is possible to print a bar code on the obverse side as well (shown as 5). Error prevention is assured by check digits encoded into both bars so that the software which reads the bar code can determine that the information from two reads (front and back) is in fact from the same strip test. Additionally, the obverse side could also be used to attach a bar code label marked with an appropriate patient identification code. It would also be possible to place bar codes in more than one, or a plurality of locations on the strip. Even in the case of a plurality of bar codes, operator intervention is minimized. In the case of two separate bar codes on opposite sides of a single strip, the bar codes may be read simultaneously by a reader equipped to scan both sides at the same time, or each side could be scanned individually for a total of two scans. It is preferred that the bar codes be proximate to one another to minimize the total number of scans.

The bar code reader, and associated decoder are connected to a computer which is a part of the LIS. Upon reading the bar code, the test information and result is appropriately decoded and entered into the LIS. Manufacturers of LIS's suitable for use in the present invention include, but are not limited to the The Digital Structures Group (Macon, Ga.), Technidata (France), and ISYS/BIOVATION (Orlando, Fla.).

Figure 2:
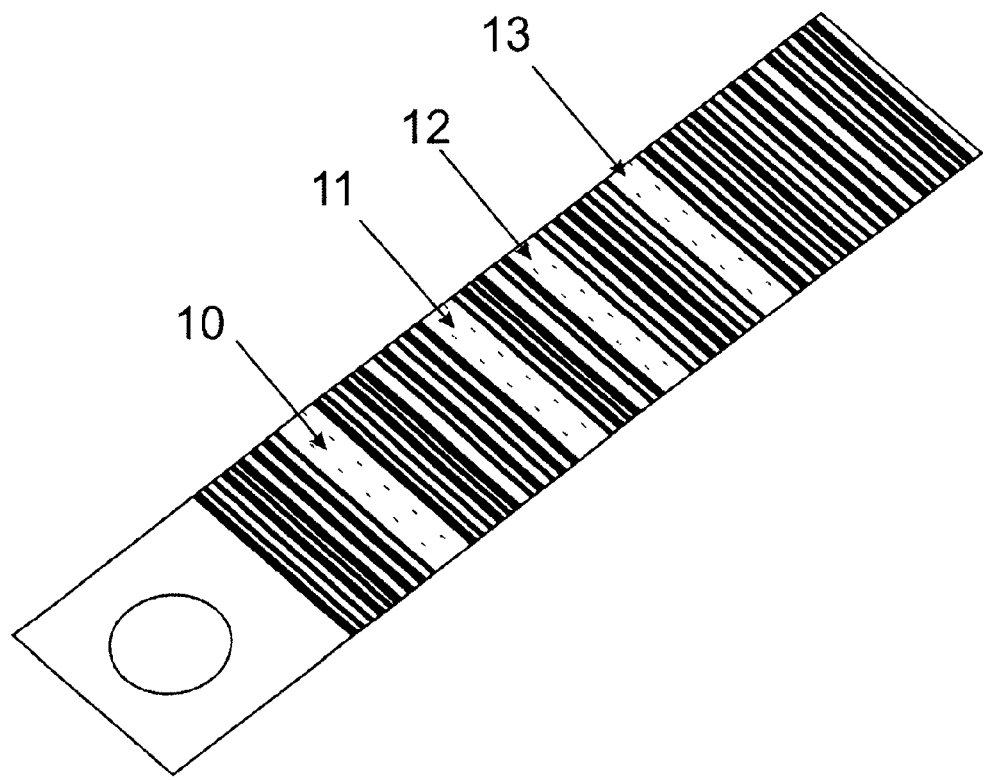
FIG. 2 shows a bar code printed strip test suitable for an assay for multiple analytes, or for the semi-quantitative assay of a single analyte.

FIG. 2 illustrates an embodiment where several results may comprise portions of the machine-readable information. The results of three different tests are encoded at three different locations (10, 11, 12), and, as before, the quality control band (13) is the most distal from the sample application area. Although the illustration shows an example of three different test zones, it should be understood that any desired number of test results may be encoded on a given strip. In this embodiment, the three test results (10, 11, 12) could be different values of the same analyte, thus allowing encoding of semi-quantitative tests. For example, if this were a test for Troponin I (cTnI) used in diagnosis of acute myocardial infarction, then band (10) could be darkened if the concentration of cTnI was >0.1 ng/mL, band (11) could be darkened if the concentration of cTnI was >1.0 ng/mL, and band (12) could be darkened if the concentration of cTnI was >2.0 ng/mL. In this way, a simple to use test could provide semi-quantitative results which could easily be machine-read and stored as part of a LIS.

Furthermore, it would be possible to combine these two concepts. For example, a test for presence of myocardial infarct might require the detection of CK-MB above a pre-defined cutoff level, as well as a test that cTnI was within two pre-defined cutoff levels. In this case, two or three of the test zones could be for cTnI with different cutoff levels, and one test zone could be for CK-MB at a single cutoff.

Although the described embodiments use a linear bar code, it will be obvious to one skilled in the art that a two dimensional bar code could be used if there was sufficient space to allow higher information density, or to incorporate test results which can not be implemented as a stripe, but appear as a dot or darkened region which can be embedded into a two dimensional bar code.

In some cases, incorporating the test results within the bar code may result in a test zone which is obscured by the bar code printing, and therefore less amenable to a visual readout. In this case, the bar code can be printed in a different color than the result band so the results are more apparent. Another alternative is to print the bar code in invisible ink, but ink which is visible in ultraviolet or infrared light, or fluorescent ink which is invisible under normal lighting but can be read when illuminated with ultraviolet light. In this case, the bar code is not visible when the test results are read by the naked eye, but are available when the strip test is read by a special bar code reader with the appropriate illumination to distinguish between the printed bars and the background.

The invention also provides methods for obtaining identifying information and the analyte assay result of a diagnostic test, comprising the steps of providing a diagnostic test device comprising: a sample zone for application of a fluid sample, at least one test zone providing reagents necessary for performing an assay for the analyte, whereby the analyte assay result may be obtained, and machine-readable information comprising identifying information and the analyte assay result; performing the analyte assay; and machine reading the machine-readable information, whereby the identifying information and analyte assay result may be obtained.

In one embodiment, the present invention provides methods for obtaining identifying information and the analyte assay result of a diagnostic strip test, comprising the steps of providing a diagnostic strip test of the present invention, performing the analyte assay, and machine reading the machine-readable information, whereby the diagnostic strip test identifying information and analyte assay result may be obtained. Many of the details of these embodiments have been described in conjunction with the description of the diagnostic test devices.

What is claimed is:

1. A diagnostic test device comprising:
    a) a sample zone for application of a fluid sample;
    b) at least one test zone having reagents necessary for performing an assay for an analyte, whereby an analyte assay result may be obtained; and
    c) machine-readable information comprising identifying information and analyte assay information capable of indicating said analyte assay result said machine-readable information comprising identifying information and analyte assay information are located in the same position in said test zone;
    wherein said analyte assay result is indicated by an alteration of existing machine-readable information.

2. The diagnostic test device of claim 1, wherein the machine-readable information is a bar code.

3. The diagnostic test device of claim 2, further comprising machine readable information in a plurality of locations on the test device.

4. The diagnostic test device of claim 2, wherein the bar code is a two-dimensional bar code.

5. The diagnostic test device of claim 1 further comprising more than one test zone, wherein each test zone provides the reagents necessary for performing an assay for the presence of a different analyte.

6. The diagnostic test device of claim 1 further comprising more than one test zone, wherein each test zone provides the reagents necessary for performing an assay for the presence of a different amount of analyte.

7. The diagnostic test device of claim 1, wherein the machine-readable information is printed in invisible ink.

8. The diagnostic test device of claim 1, wherein the diagnostic test device provides a visible test result.

9. The diagnostic test device of claim 1, further comprising at least one quality control zone in fluid communication with the sample zone comprising an indicator reagent for confirming the completion of the assay.

10. The diagnostic test device of claim 1, wherein the machine readable information is selected from the group consisting of MICR, OCR, a fluorophore, a chromophore, a radioisotope, a dye, colloidal gold, colloidal carbon, a latex particle, and a chemiluminescent agent.

11. A diagnostic strip test comprising at least one flow path, each flow path comprising;
    a) a sample zone for application of a fluid sample;
    b) at least one test zone in fluid communication with the sample zone, the test zone of each flow path having reagents necessary for performing an assay for the presence of an analyte, whereby an analyte assay result may be obtained; and
    c) machine-readable information comprising identifying information and analyte assay information capable of indicating said analyte assay result, said machine-readable information comprising identifying information and analyte assay information are located in the same position in said test zone;
    wherein said analyte assay result is indicated by an alteration of existing machine-readable information.

12. A method for obtaining identifying information and the analyte assay result of a diagnostic test, comprising the steps of:
    a) providing a diagnostic test device comprising:
        i) a sample zone for application of a fluid sample;
        ii) at least one test zone having reagents necessary for performing an assay for the analyte, whereby the analyte assay result may be obtained; and
        iii) machine-readable information comprising the identifying information and analyte assay information capable of indicating the analyte assay result, said machine-readable information comprising identifying information and analyte assay information are located in the same position in said test zone;
    b) performing the analyte assay; and
    c) machine reading the machine-readable information;
    whereby the identifying information and the analyte assay result may be obtained, wherein said analyte assay result is indicated by an alteration of existing machine-readable information.

13. The method of claim 12, wherein the machine-readable information is a bar code printed on one side of a strip test.

14. The method of claim 13, wherein the bar code is linear.

15. The method of claim 13, wherein the bar code is two dimensional.

16. The method of claim 13, wherein the bar code is printed in invisible ink.

17. The method of claim 12, wherein the machine-readable information is detectable by optically scanning.

18. The method of claim 12, wherein the diagnostic test device further comprises machine readable information in a plurality of locations on the test device.

19. The method of claim 12, further comprising more than one test zone, wherein each test zone provides the reagents necessary for performing an assay for the presence of a different analyte.

20. The method of claim 12, further comprising more than one test zone, wherein each test zone provides the reagents necessary for performing an assay for the presence of a different amount of a desired analyte.

21. The method of claim 12, further comprising more than one test zone, wherein a first set of test zones provides the reagents necessary for performing an assay for the presence of one or more different analytes, and a second set of test zones provides the reagents necessary for performing an assay for the presence of a different amount of said one or more different analytes.

22. The method of claim 12, wherein the assay result is visible.

23. The method of claim 12, wherein step (c) further comprises decoding the machine-readable information and entering the identifying information and the analyte assay result in a laboratory information system.

24. The method of claim 12, wherein the diagnostic strip test further comprises at least one quality control zone in fluid communication with the sample zone comprising an indicator reagent for confirming the completion of the assay.

25. The method of claim 12, wherein the machine readable information is selected from the group consisting of MICR, OCR, a fluorophore, a chromophore, a radioisotope, a dye, colloidal gold, colloidal carbon, a latex particle, and chemiluminescent agent.

26. A method for obtaining identifying information and the analyte assay result of a diagnostic strip test, comprising the steps of:

a) providing a diagnostic strip test comprising at least one flow path, each flow path comprising:

i) a sample zone for application of a fluid sample;

ii) at least one test zone in fluid communication with the sample zone, the test zone of each flow path having reagents necessary for performing an assay for the analyte, whereby the analyte assay result may be obtained; and iii) machine-readable information comprising the identifying information and the analyte assay information capable of indicating analyte assay result, said machine-readable identifying information and analyte assay information are located in the same position in said test zone;

b) performing the analyte assay; and c) machine reading the machine-readable information;

whereby the diagnostic strip test identifying information and analyte assay result may be obtained; wherein said analyte assay result is indicated by an alteration of existing machine-readable information.

\* \* \* \* \*